US00PP14893P2

(12) United States Plant Patent
Whetman

(10) Patent No.: US PP14,893 P2
(45) Date of Patent: Jun. 8, 2004

(54) DIANTHUS PLANT NAMED 'DEVON WINNIE'

(50) Latin Name: *Dianthus×hybrida*
Varietal Denomination: Devon Winnie

(76) Inventor: John Whetman, Deer Park Farm, Chudleigh, Devon TQ13 ONH (GB)

( * ) Notice: Subject to any disclaimer, the term of this patent is extended or adjusted under 35 U.S.C. 154(b) by 0 days.

(21) Appl. No.: 10/676,191

(22) Filed: Sep. 30, 2003

(51) Int. Cl.[7] ..... A01H 5/00
(52) U.S. Cl. ..... Plt./283
(58) Field of Search ..... Plt./283

*Primary Examiner*—Anne Marie Grunberg
*Assistant Examiner*—Annette H Para

(57) ABSTRACT

A new cultivar of Dianthus plant named 'Devon Winnie' that is characterized by compact mounding habit, blue-green foliage and moderately fragrant dark pink flowers. In combination these traits set 'Devon Winnie' apart from all other existing varieties of Dianthus known to the inventor.

2 Drawing Sheets

Genus: Dianthus.
Species: ×*hybrida*.
Denomination: Devon Winnie.

BACKGROUND OF THE INVENTION

The present invention relates to a new and distinct cultivar of carnation that is grown for use as an ornamental container plant. It is known botanically as 'Devon Winnie'.

'Devon Winnie' is a hybrid plant that is the product of a breeding program started by the inventor in 1980. The breeding program is not federally funded and is on going, conducted in a cultivated area of Houndspool, Dawlish, Devon, United Kingdom. The primary focus of the breeding program is to produce new cultivars of carnations that exhibit unique growth habit.

'Devon Winnie' is a hybrid plant that was selected in 2000, from a large group of open pollinated seedlings. 'Devon Winnie' was selected by the inventor for the distinguishing traits of, prominently early flowering, compact habit, large double flowers, perfume fragrance and bright flower color. The exact parents of 'Devon Winnie' are unknown. The female parent plant is presumed to be an unknown cultivar of Dianthus (unpatented). The male parent plant is presumed to be an unknown cultivar of Dianthus (unpatented). The differences between the instant plant and the parent plants, is unknown to the inventor. There is no comparison plant known to the inventor.

Asexual reproduction of the new cultivar was first accomplished by the inventor in 2000 in a cultivated area of Houndspool, United Kingdom. The method of asexual propagation used was stem cuttings. Since that time the characteristics of the new cultivar have been determined stable and are reproduced true to type in successive generations by vegetative propagation.

SUMMARY OF THE INVENTION

The following traits have been repeatedly observed and represent the characteristics of the new Dianthus cultivar 'Devon Winnie'. These traits in combination distinguish this cultivar from all other commercial varieties known to the inventor. 'Devon Winnie' has not been tested under all possible conditions and phenotypic differences may be observed with variations in environmental, climatic and cultural conditions, without however any change in genotype.

1. Dianthus 'Devon Winnie' exhibits a compact mounding growth habit.
2. Dianthus 'Devon Winnie' exhibits large moderately fragrant dark pink flowers.
3. Dianthus 'Devon Winnie' exhibits blue-green foliage.
4. Dianthus 'Devon Winnie' is 15–20 cm. in height and 10–15 cm in width in a 1.5-liter container.
5. Dianthus 'Devon Winnie' is an evergreen perennial herb.
6. Dianthus 'Devon Winnie' blooms from March to November.
7. Dianthus 'Devon Winnie' is hardy to minus 15° Centigrade

BRIEF DESCRIPTION OF THE DRAWINGS

The accompanying color drawings illustrate the overall appearance of the new Dianthus variety 'Devon Winnie' showing colors as true as it is reasonably possible to obtain in colored reproductions of this type. Colors in the drawings may differ from the color values cited in the detailed botanical description, which accurately describe the actual colors of the new variety 'Devon Winnie'.

The drawing on sheet 1 illustrates the entire plant in flower. This drawing was made of 6-month-old plants grown in 6 inch containers under a roof-vented polythene hoop house in Lompoc, Calif. No chemicals were used to treat the plants.

The drawing on sheet 2 is a close-up view of a typical flower.

The sheet 2 drawing were made of plants grown in a 4" containers under a cold glasshouse in Houndspool, Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Devon Winnie'. Data was collected from plants grown in 1.5-liter containers under a cold glasshouse in Houndspool, United Kingdom. The color determinations are in accordance with the 2002 edition of The Royal Horticultural Society Colour Chart of The Royal Horticultural Society, London, England, except when general color terms of ordinary dictionary significance are used. No chemicals were used to treat the plants. Growing conditions are typical to other Dianthus.

Botanical classification: Dianthus 'Devon Winnie'.
Species: *xhybrida.*
Common name: Hybrid pink carnation.
Commercial classification: Hardy perennial herb.
Use: Ornamental plant for small pots and containers.
Parentage: 'DEVON WINNIE' is a hybrid plant that resulted from the open pollination of a group of unidentified seedlings. The exact parents are unknown:
- *Presumed female parent plant.*—Unknown cultivar of Dianthus cultivar.
- *Presumed male parent plant.*—Unknown cultivar of Dianthus cultivar.

Plant description:
- *Bloom period.*—March to November.
- *Plant habit.*—Compact mounding habit.
- *Plant height.*—15–20 cm. in height.
- *Plant width.*—10–15 cm. in width.
- *Plant hardiness.*—Hardy to minus 15° Centigrade.
- *Type.*—Perennial evergreen herb.
- *Root system.*—Fibrous.
- *Propagation.*—Propagation is accomplished using stem cuttings.
- *Culture requirements.*—Plant in full sun, well-drained and moderately fertile soil and keep well fertilized and watered.
- *Diseases and pests.*—Susceptible to known Dianthus pests and disease but no other susceptibilities to pests or disease are known to the inventor.
- *Time required to produce a rooted cutting.*—2 weeks are needed to produce a rooted cutting and 5 weeks are needed to produce a rooted plug.
- *Temperature recommended for cuttings to produce roots.*—The temperatures needed to produce a rooted cutting is a minimum of 15° Centigrade air temperature and base heat of 21° Centigrade.
- *Crop time.*—4–6 months is needed to produce a finished 1.5-liter container size from a well-rooted cutting.

Stem:
- *Shape.*—Cylindrical.
- *Stem dimensions.*—20 cm. in length and 2 mm. in diameter.
- *Stem surface.*—Glabrous and glaucous.
- *Stem color.*—122A.
- *Branching.*—Numerous basal breaks and racemose inflorescence.
- *Internode length.*—15–50 mm, between nodes.
- *Node dimensions.*—3 mm. in diameter and 5 mm. in length.
- *Node color.*—144C.

Foliage:
- *Type.*—Evergreen.
- *Shape.*—Lanceolate.
- *Division.*—Simple.
- *Apex.*—Acute.
- *Base.*—Decurrent.
- *Venation.*—Not prominent.
- *Margins.*—Entire.
- *Attachment.*—Sheathing.
- *Arrangement.*—Opposite and spiraling up stem.
- *Surfaces* (*adaxial and abaxial*).—Glaucous.
- *Leaf dimensions.*—5–6.5 cm. in length and 4–5 mm. in width.
- *Leaf color* (*adaxial surfaces*).—122A.
- *Leaf color* (*abaxial surfaces*).—122B.
- *Stipules.*—Present.
- *Stipule dimensions.*—2–3 mm. in width and 15–20 mm. in length.
- *Stipule color.*—122A.
- *Anthocyanin.*—Absent.
- *Fragrance.*—Absent.

Flowers:
- *Inflorescence.*—Raceme with branches.
- *Flower type.*—Double and symmetrical.
- *Flower shape.*—Salviform.
- *Flower dimensions* (*including calyx*).—25–30 mm. in length and 25–35 mm. in diameter.
- *Bud color.*—Each bud is N139C on apical half and 13A on basal half.
- *Anthocyanin.*—Present.
- *Bud dimensions.*—20 mm. in length and 8 mm. in width.
- *Bud shape.*—Cylindrical.
- *Petals.*—Persistent double petals, apopetalous, overlapping and sympetalous.
- *Petal number.*—2–30 petals in number and 5 petaloid stamens.
- *Petal dimensions* (*outer whorl*).—30 mm. in length and 17 mm. in width.
- *Petal margin.*—Dentate (toothed 2 mm deep).
- *Petal shape.*—Obdeltoid
- *Petal color* (*adaxial surface*).—Colors N66C, 71A, 155A and 145A, 60A are each individually present on each individual petal.
- *Petal color* (*abaxial surface*).—Colors 149D, 155A and N66D are each individually present on each individual petal.
- *Petal surfaces* (*adaxial and abaxial*).—Glabrous.
- *Calyx dimensions.*—10 mm. in width and 15 mm. in length.
- *Sepal color* (*adaxial surfaces*).—N138C.
- *Sepal color* (*abaxial surfaces*).—139D.
- *Sepal surface.*—Glaucous.
- *Sepal apex.*—Acuminate.
- *Anthocyanin.*—Absent.
- *Sepal number.*—5 in number.
- *Fused or unfused.*—Fused.
- *Epicalyx.*—4 bracts in number.
- *Epicalyx dimensions.*—6 mm. in length and 3 mm. in diameter.
- *Epicalyx color* (*adaxial surfaces*).—N138C.
- *Epicalyx color* (*abaxial surfaces*).—139D.
- *Peduncle dimensions.*—15–70 mm. in length and 1 mm. in diameter.
- *Peduncle color.*—122A.
- *Peduncle surface.*—Glaucous.
- *Fragrance.*—Moderate perfume fragrance.
- *Lastingness of flower.*—Each individual flower lasts 10 days at 20° Centigrade.

Reproductive organs:

*Stamens.*—5 in number.

*Stamen color.*—N66D.

*Stamen dimensions.*—10–12 mm. in length and 1 mm. in diameter.

*Anther color.*—N66D.

*Anther dimensions.*—2 mm. in length and 0.5 mm. in diameter.

*Anther attachment.*—Basafixed.

*Pollen color.*—N66D.

*Quantity of pollen.*—Small amount.

*Styles.*—Two in number.

*Style dimensions.*—20 mm. in length and 1 mm. in width.

*Style color.*—N66D.

*Stigma.*—Single stigma.

*Color of stigma.*—N66D.

*Height of stigma above petals* (*at maturity*).—Exserted 10 mm. above petals.

*Pistils.*—Two in number.

*Pistil shape.*—Thread-like.

*Ovary position.*—Superior.

*Ovary dimensions.*—5 mm in length and 4 mm. in diameter.

*Ovary shape.*—Spindle shaped.

*Ovary color.*—144D.

Seed:

*Seed color.*—202A.

*Seed dimensions.*—2 mm. in length and 1 mm. in width.

What is claimed is:

1. A new and distinct cultivar of Dianthus plant named 'Devon Winnie' as described and illustrated herein.

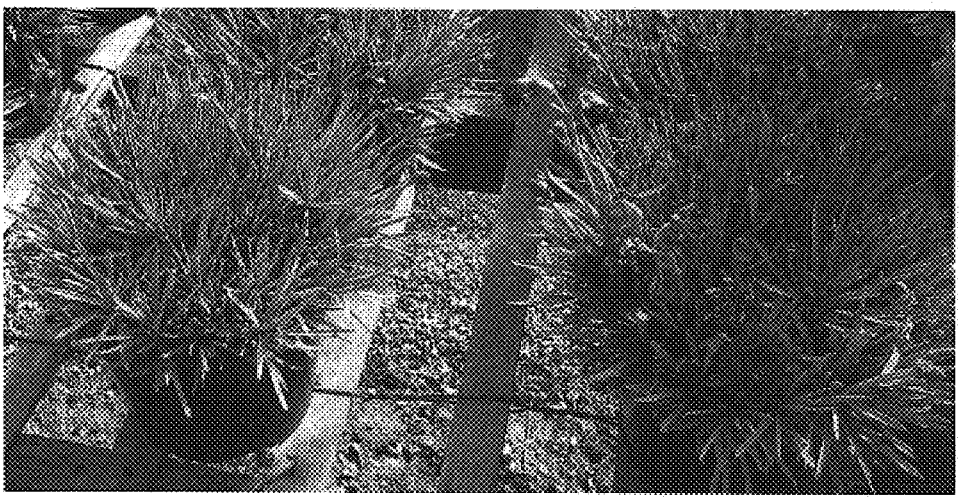

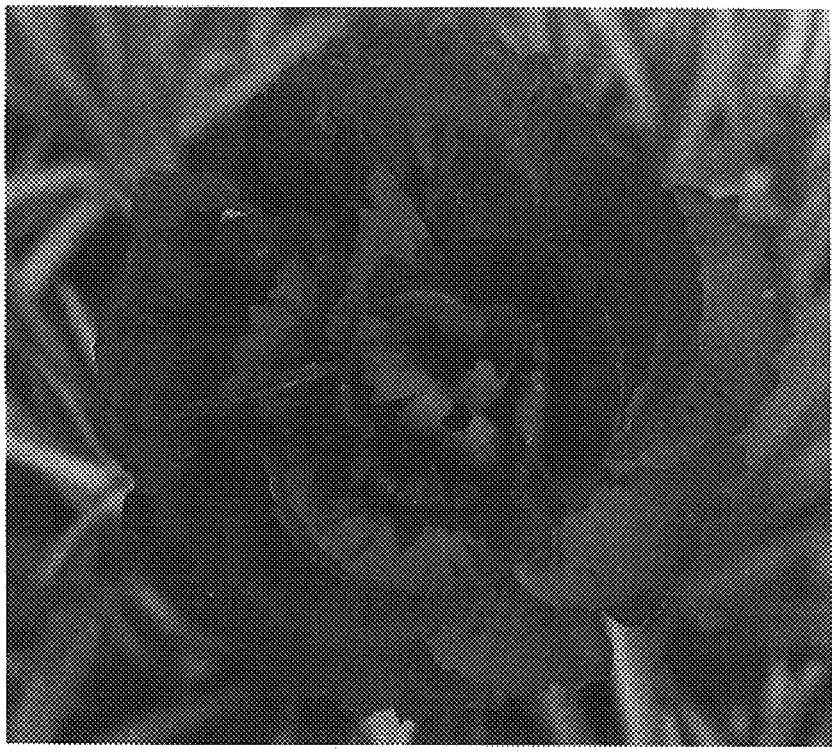

* * * * *